United States Patent [19]

Frey

[11] 4,227,265
[45] Oct. 14, 1980

[54] BONE IMPLANT WITH PLASTIC INSERT BETWEEN ELEMENTS OF DIFFERENT MECHANICAL PROPERTIES

[75] Inventor: Otto Frey, Winterthur, Switzerland

[73] Assignee: Sulzer Brothers Limited, Winterthur, Switzerland

[21] Appl. No.: 908,688

[22] Filed: May 23, 1978

[30] Foreign Application Priority Data

May 23, 1977 [CH] Switzerland .................. 6310/77

[51] Int. Cl.³ .................................. A61F 1/03
[52] U.S. Cl. ............................. 3/1.913; 3/1.9; 128/92 CA; 85/83; 403/255; 403/263; 403/361
[58] Field of Search .............. 3/1.913, 1.912, 1.9, 3/1.91, 1.911; 128/92 CA; 403/253, 254, 255, 361, 365, 263

[56] References Cited

U.S. PATENT DOCUMENTS

| | | | |
|---|---|---|---|
| 2,358,737 | 9/1944 | Schwinn | 403/365 X |
| 3,171,321 | 3/1965 | Fischer | 85/83 |
| 3,199,398 | 8/1965 | Weisz | 85/83 |
| 3,596,656 | 8/1971 | Kaute | 128/92 D |
| 3,707,006 | 12/1972 | Bokros et al. | 128/92 CA X |
| 3,894,297 | 7/1975 | Mittlemeier et al. | 128/92 CA X |
| 4,085,652 | 4/1978 | Vanotti | 85/83 |

FOREIGN PATENT DOCUMENTS 2618763  11/1976  Fed. Rep. of Germany ............. 3/1.91

*Primary Examiner*—Clifford D. Crowder
*Attorney, Agent, or Firm*—Kenyon & Kenyon

[57] ABSTRACT

The bone implant is made from elements which have different mechanical properties and which are maintained out of contact from each other by means of a plastic member. The plastic member is disposed in and fills a gap formed by the implant elements. In addition, the plastic member has thin-walled extensions which are engaged in narrowing sections at the outer boundaries of the gap. These extensions guard against any creep in the plastics member under the forces imposed on the plastics member during stressing of the bone implant.

11 Claims, 4 Drawing Figures

BONE IMPLANT WITH PLASTIC INSERT BETWEEN ELEMENTS OF DIFFERENT MECHANICAL PROPERTIES

This invention relates to a bone implant construction. More particularly, this invention relates to a bone implant construction constructed of elements of different mechanical properties.

As is known, bone implants, particularly those used for a composite endoprosthesis, are frequently made of elements having different mechanical properties. For example, one element may be made of a bioceramic material or pyrolytic material while the other is made of a metal or metal alloy material. In other cases, the elements may have different hardness, different co-efficients of expansion, different surface textures, and/or different resilience. Because of the differences in mechanical properties, these elements may experience increased wear or similar unacceptable phenomena during use if there is direct contact between the elements. Thus, in order to preclude direct contact between such elements, it is known to separate the elements from each other by the use of an intermediate plastic member, for example made of polyethylene which is well known in the implant art. Such constructions are known from Swiss Pat. Nos. 533,982 and 568,753 and U.S. Pat. No. 3,707,006.

However, it has been found that the intermediate plastic members used in these implant constructions tend to creep under load. As a result, in the course of time, the incompatible materials start to contact one another directly.

Accordingly, it is an object of the invention to inhibit any cold plastic creep in an intermediate plastic member between two elements of a bone implant construction of different mechanical properties.

It is another object of the invention to preclude contact between elements of different mechanical properties in a bone implant construction over extended periods of loading.

Briefly, the invention provides a bone implant construction which is comprised of a pair of elements of different mechanical properties and a plastic member disposed between the elements. In particular, the two elements are disposed to transfer loading forces therebetween and are further disposed to define a shaped gap therebetween with narrowing sections at the exposed boundaries of the gap. These narrowing sections extend at least substantially in the direction of the loading forces. The plastic member is confined in the gap to maintain the elements out of contact with each other and has thin-walled extensions engaged in the narrowing gap sections.

The presence of the narrowing sections between the two elements of different or incompatible mechanical properties at the exposed boundaries of the gap and the thin-walled extensions of the plastic member preclude cold plastic creep of the plastic member since the gap-engaged extensions distort resiliently. That is, when the loading of the extension length-wise of the gap ceases, the extensions resume their original shape.

In order to facilitate the resilient distortion of the plastic member and of the extensions, and to further facilitate engagement of the plastic member in the gap, the boundaries of the elements defining the gap between the elements extend at least partly conically in the direction of the shear forces acting on the plastic member. In order to permit use of a relatively short overall length of the gap and of the plastic member, the transition to each narrowing section of the gap is abrupt. For example, the transition is formed by a shoulder or the like on the respective element.

Advantageously, the width of the narrowing gap sections and the thickness of the thin-walled extensions of the plastic member are chosen in dependence upon the properties of the plastic member so that the extensions distort at least substantially resiliently in the direction of the narrowing sections under load.

The elements of the bone implant may be made of a bioceramic or pyrolytic carbon on the one hand and a metal or metal alloy on the other hand. Generally, a ceramic-metal composite prothesis is preferred. Also, the plastic member can be made of ultra-high molecular weight polyethylene.

These and other objects and advantages of the invention will become more apparent from the following detailed description taken in conjunction with the accompanying drawings wherein.

Figure 1:
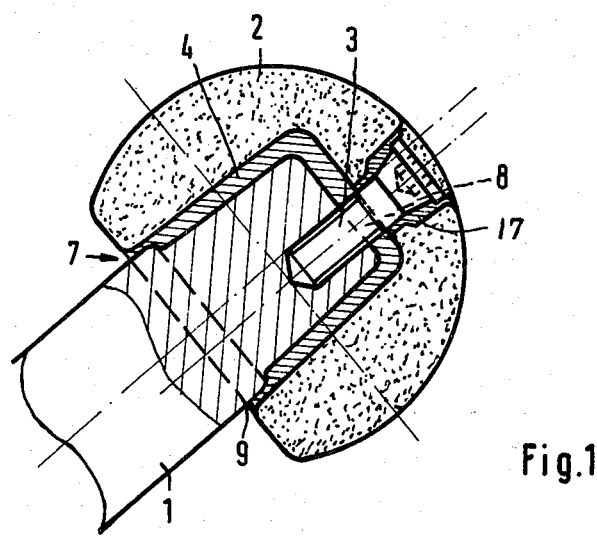
FIG. 1 illustrates a longitudinal sectional view of a bone implant utilizing a plastic member in accordance with the invention.

Referring to FIG. 1, the bone implant, for example for a hip joint, includes a metal element having a stem 1 and a bioceramic spherical element in the form of a joint head 2. The joint head 2 has a cavity which is sized to receive the stem 1 in spaced relation so as to define a cup-shaped gap 8 therebetween while a metal anchoring screw 3 serves to secure the joint head 2 to the stem 1. As indicated, the axis of the screw 3 is offset relative to the axis of the stem 1. In addition, the bone implant has a cup-shaped plastic member 4 disposed in the gap 8 between the stem 1 and joint head 2. The plastic member 4 is of a size to maintain the joint head 2 and stem 1 out of contact with each other. As shown in FIG. 1, the plastic member 4 has a circular cylindrical portion to surround the stem 1 and a base portion which is provided with an aperture 5 for passage of the anchoring screw 3.

Figure 2:
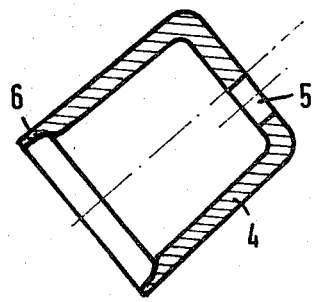
FIG. 2 illustrates a cross-sectional view of the plastic member of FIG. 1.

Referring to FIGS. 1 and 2, the plastic member 4 is also provided at the terminal end or outer boundary with a narrowed thin-walled extension 6 coaxially with the cylindrical portion of the plastic member. This extension 6 is sized to fit into a narrowing section 7 at the bottom terminal portion of the gap 8 between the joint head 2 and the stem 1. As shown in FIG. 1, the narrowing section 7 extends in a direction parallel to the axis of the stem 1 and is formed by a shoulder 9 on the stem 1 which projects radially outwardly towards the joint head 2. This direction of the narrowing section 7 is the preferred direction for relative movement of the joint head 2 on the stem 1 and for the shear forces operative on the plastic member 4.

During use, when forces are imposed on the joint head 2 and stem 1 to move the joint head 2 and stem 1 relative to each other, the plastic member 4 is able to distort resiliently. In addition, the thin-walled extensions 6 within the narrowing section 7 of the gap 8 are also able to distort resiliently. This precludes any plastic fill or creep of the plastic member which may lead to the stem 1 and joint head 2 making direct contact with one another over the course of time. That is the plastic member 4 remains confined in the gap 8 between the head 2 and stem 1.

Figure 3:
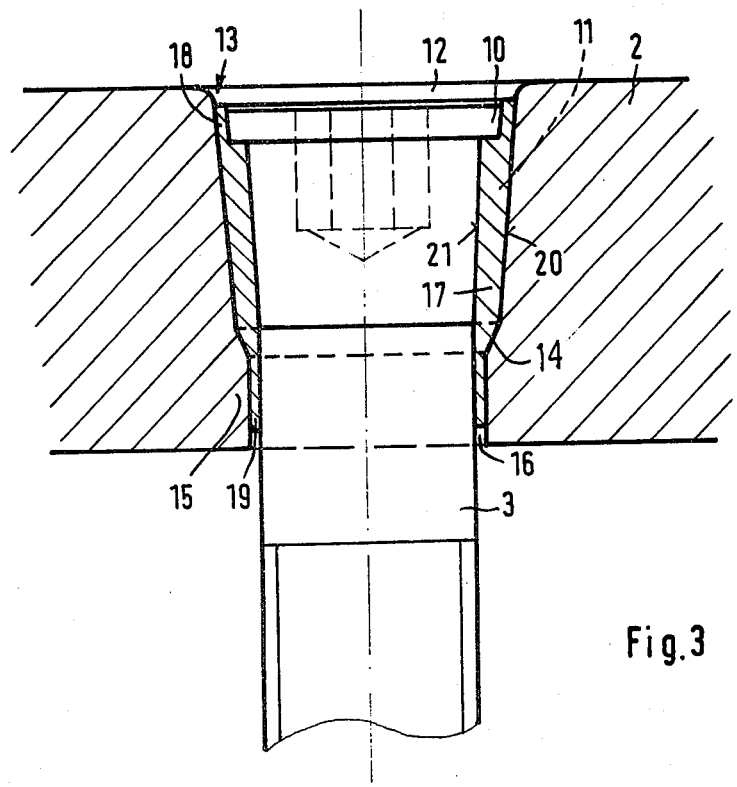
FIG. 3 illustrates a further embodiment of a plastic member of a bone implant construction in accordance with the invention.

Referring to FIG. 1, the implant construction may also have a plastic member 17 of cylindrical or sleeve shape between the anchoring screw 3 and the joint head 2. As shown in FIG. 3, the anchoring screw 3 has a head which is formed with a circumferential shoulder 10 which projects outwardly into a gap 11 which remains when the screw 3 has been engaged in a bore 12 in the joint head 2. This gap 11 terminates at the bottom in a narrow section 16 which is disposed substantially coaxially of the screw 3 and, thus, in the preferred direction of relative movement between the screw 3 and the joint head 2. The narrow section 16 is formed by virtue of a narrow circumferentially shoulder 15 of the spherical joint head 2 which projects into the bore 12. As shown in FIG. 3, this narrow section 15 adjoins a conical transition portion 14 of the gap 11. In addition, a circumferential shoulder 10 is formed on the screw 3 which projects outwardly into the gap 11 so as to narrow the gap 11 at the opposite end of the plastc member 17.

Figure 4:
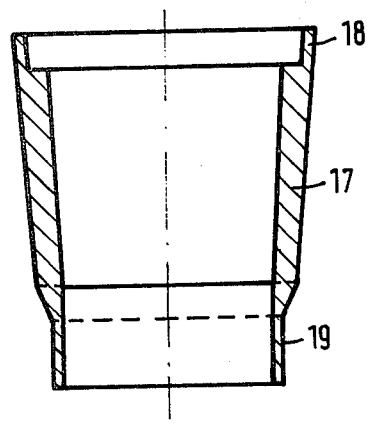
FIG. 4 illustrates a cross-sectional view of the plastics member of FIG. 3.

As shown in FIGS. 3 and 4, the plastic member 17 has a circular cylindrical portion to surround the screw 3 and thin-walled extensions 18, 19 at opposite ends of the cylindrical portion. These extensions 18, 19 are coaxial of the axis of the hollow plastic member 17 and are sized to be engaged in the narrow sections 13, 16 between the anchoring screw 3 and the joint head 2 within the gap 11. In this regard, the boundary surfaces 20, 21 of the joint head 2 and screw 3 along the gap 11 are conical over at least some of their length. This facilitates engagement and the resilient distortion of the plastic member 17 in response to loadings and variations in loading occurring substantially in the direction of the axis of the screw 3.

The plastic member 17 may, of course, be used between any two elements of a bone implant which are made of different mechanical properties.

What is claimed is:

1. A bone implant construction comprising
a pair of elements of different mechanical properties disposed in relative movable relation, said elements being disposed to transfer loading forces therebetween and to define a shaped predetermined gap therebetween with an abrupt transition to a narrowing section at at least one end of said gap, said section extending at least substantially in the direction of said loading forces; and
a resiliently distortable removable plastic member confined in said gap to maintain said elements out of contact with each other, said plastic member having a cylindrical portion to surround one element and a narrowed thin-walled extension coaxial with said cylindrical portion and engaged in said narrowing section to inhibit cold plastic creep of said cylindrical portion from said gap at said one end.

2. A bone implant construction as set forth in claim 1 wherein said elements are disposed to impart a shear force on said plastic member and extend in the plane of said shear force.

3. A bone implant construction as set forth in claim 1 wherein at least one of said elements has a shoulder directed into said gap in abutment with said plastic member to abruptly narrow said gap at said narrowing section.

4. A bone implant construction as set forth in claim 1 wherein said elements and said plastic member are sized relative to each other to permit said thin-walled extension to resiliently distort in the direction of said narrowing section under load.

5. A bone implant construction as set forth in claim 1 wherein one of said elements is made of a bioceramic material and the other of said elements is made of metal.

6. A bone construction comprising
a first element having a stem;
a second element having a cavity receiving said stem of said first element in relative movable relation, said second element being spaced from said first element to define a predetermined cup-shaped gap therebetween with a narrowing section at an end of said gap; and
a resilient cup-shaped plastic member removably disposed in said gap between said elements to maintain said elements out of contact with each other, said plastic member having a circular cylindrical portion in said gap and a narrowed thin-walled extension coaxial with said cylindrical portion engaged in said narrowing section.

7. A bone implant construction as set forth in claim 6 wherein said stem has a circumferential shoulder projecting outwardly into said gap to abut said plastic member and narrow said gap at said narrowing section.

8. A bone implant construction as set forth in claim 6 wherein said stem is made of metal and said second element is made of bioceramic material.

9. A bone implant construction comprising
a first element;
a second element having a cavity receiving said first element in relative movable relation, said second element being spaced from said first element to define a predetermined annular gap therebetween with a narrowing section at opposite ends of said gap; and
an annular resilient plastic member removably disposed in said gap between said elements to maintain said elements out of contact with each other, said plastic member having a circular cylindrical portion to surround said first element and a narrowed thin-walled extension coaxial with and at each end of said cylindrical portion engaged in a respective narrowing section.

10. A bone implant construction as set forth in claim 9 wherein said first element has a circumferential shoulder projecting outwardly into said gap to abut said plastic member and narrow said gap at one of said narrowing sections and said second element has a circumferential shoulder projecting inwardly into said gap to abut said plastic member and narrow said gap at the opposite narrowing section.

11. A bone implant construction as set forth in claim 10 wherein one of said elements is made of metal and the other of said elements is made of bioceramic material.

* * * * *